United States Patent [19]

Kuisl et al.

[11] Patent Number: 4,490,678
[45] Date of Patent: Dec. 25, 1984

[54] METHOD OF AND AN APPARATUS FOR MEASURING ION CONCENTRATIONS IN SOLUTIONS

[75] Inventors: Max Kuisl, Ulm; Manfred Klein, Heroldstatt, both of Fed. Rep. of Germany

[73] Assignee: Licentia Patent-Verwaltungs-G.m.b.H., Frankfurt am Main, Fed. Rep. of Germany

[21] Appl. No.: 377,985

[22] Filed: May 13, 1982

[30] Foreign Application Priority Data

May 15, 1981 [DE] Fed. Rep. of Germany ....... 3119419
Dec. 24, 1981 [DE] Fed. Rep. of Germany ....... 3151325

[51] Int. Cl.³ .............................................. G01N 27/56
[52] U.S. Cl. ................................... 324/438; 324/450; 204/412
[58] Field of Search ................. 324/51, 425, 438, 439, 324/441, 447, 450; 357/25; 204/416, 433, 412

[56] References Cited

U.S. PATENT DOCUMENTS

| 3,512,080 | 5/1970 | Hanson | 324/450 |
| 3,862,895 | 1/1975 | King et al. | 204/195 |
| 4,332,658 | 6/1982 | Tsuboshima | 324/425 |

FOREIGN PATENT DOCUMENTS

| 0010035 | 11/1980 | European Patent Off. . |
| 1297359 | 6/1969 | Fed. Rep. of Germany . |
| 2618738 | 10/1977 | Fed. Rep. of Germany . |
| 1111516 | 5/1968 | United Kingdom . |

OTHER PUBLICATIONS

"Ion-Sensitive Field Effect Transistors", Janata et al., *Ion-Selective Electrode Review*, vol. 1, 1979, pp. 31–79.

Primary Examiner—Michael J. Tokar
Assistant Examiner—Kevin D. O'Shea
Attorney, Agent, or Firm—Spencer & Frank

[57] ABSTRACT

A method of measuring ion concentrations in solutions comprises using at least two ion sensitive test electrodes in the solution to be measured, the test electrodes having different sensitivities only in respect of the ion or ion mixture to be measured, setting the operating point of the test electrodes by means of at least one common reference electrode, and evaluating the signals of the test electrodes to produce a measurement result essentially independent of the properties of the reference and test electrodes which would interfere with accurate measurement.

The invention also includes apparatus suitable for carrying out the method.

17 Claims, 3 Drawing Figures

METHOD OF AND AN APPARATUS FOR MEASURING ION CONCENTRATIONS IN SOLUTIONS

BACKGROUND OF THE INVENTION

The invention relates to a method of and an arrangement for testing ion concentrations in solutions using ion sensitive test and reference electrodes.

In many cases electrochemical processes are used in order to determine ion concentrations in a solution. Potential measurement with ion selective electrodes is a testing technique which is easy to manipulate and adapted to modern electronics. Ion-selective electrodes are electrochemical half cells in which there is a potential difference at the phase boundary between the electrode material and the electrolyte. This potential difference $\Delta\psi$ is related to the concentration (more precisely activity) of the type of ions to which the electrode is to be sensitive. In theory this relationship is substantiated by Nernst's equation:

$$\Delta\psi = \Delta\psi_o + (RT/zF)\ln a_{Me^{z+}}(1),$$

where T is the absolute temperature, R is the molar gas constant, F is the Faraday constant and z is the valency of the particular type of ions $Me^{z+}$. $\Delta\psi_o$ is the potential of the cell half for the ion activity $a_{me^{z+}} = 1$. The potential $\Delta\psi_o$ is called the standard potential. A plurality of ion sensitive electrodes are known. Not only is it possible to determine simple inorganic ions but also those of amino acids and complex organic compounds such as enzymes and proteins, for example.

Potential measurements in electrochemistry are carried out by measuring the potential difference between a test electrode and a reference electrode. In addition the test electrode should respond as selectively as possible to the ion which is to be investigated. On the other hand the reference electrode should not be sensitive to impurities in the test solution (electrolyte). In some circumstances the two electrodes have to be dipped into separate electrolytes, a test electrolyte and a reference electrolyte (standard solution), the latter being connected by means of a so-called current key. A current "key" consists of a curved glass tube or capillary which connects the two electrolytes and contains a salt solution the cations and anions of which have the same mobility. Such an arrangement is very expensive.

It has been proved by experience in electrochemistry that the values for the absolute potentials at these electrodes, more particularly at ion-sensitive electrodes, exhibit disruptive fluctuations caused, for example, by undesirable chemical changes in the electrodes. Therefore it is usual to calibrate with the aid of a standard solution each time before using an electrode. However the relative dependence of the potential on the activity of the ion which is to be measured doesn't change significantly in time. In a number of electrodes the value predetermined by Nernst's equation is even achieved. Therefore one calibration point only is frequently determined for series tests, the one calibration point fixing the absolute amount of the potential, whereas the manufacturers' specifications are relied upon for the dependence of the potential on concentration or a dependence in accordance with Nernst's equation is stipulated. The properties of both electrodes are included in measurement of potential as well as the properties of the test and reference electrodes. In the case of reference electrodes, fluctuations in the (reference) potential of approximately 5% can occur.

A so-called ion-sensitive field effect transistor (ISFET) can be used as the test electrode and is described for example in the journal *Ion-Selective Electrode Review*, Vol. 1, 1979, pages 31 to 79, J. Janata and R. J. Huber "Ion-sensitive Field Effect Transistors".

These ion-sensitive field effect transistors (ISFETs) also make it possible to transform the ion concentrations of a solution into an electrical signal. In addition, a potential difference is formed between the solution and the ion-sensitive gate of the ISFETs. However, this potential difference is not measured directly; instead the drain/source current of the ISFETs which is affected thereby is measured. The drain/source current of the ISFET is therefore a measure of the electrical potential at the gate electrode which is in direct contact with the electrolyte to be measured. However, a reference electrode which determines the gate potential is necessary in this case, too, as a reference and in order to fix the operating point. Ultimately therefore, the accuracy and reproducibility of the reference electrode is decisive in the use of ISFETs. Therefore, there is no basic progress to be made over the classical method of potential measurement with two electrodes, with this particular use of an ISFET as a test electrode.

SUMMARY OF THE INVENTION

It is an object of the invention to provide a method and arrangement for measuring ion concentrations in solutions which are broadly independent of reference electrodes and standard solutions for calibrating the arrangement.

According to a first aspect of the invention there is provided a method of measuring ion concentrations in solutions comprising placing at least two ion sensitive test electrodes having different sensitivities only in respect of the ion or ion mixture to be measured in the solution, setting an operating point of said tests electrodes by means of at least one common reference electrode and evaluating the output signals of said test electrodes to produce a measurement result essentially independent of the properties of said reference and test electrodes which would interfere with accurate measurement.

Further, according to this aspect of the invention, there is provided a method of measuring ion concentrations in solutions using ion-sensitive test and reference electrodes, in which at least two-ion sensitive test electrodes are used, these having different sensitivities to the concentration and/or activity only in relation compared to the ion or ion mixture to be measured. At least one common reference electrode is used which merely sets at least one operating point of the test electrodes. The output signals of the test electrodes are evaluated such that they are made essentially independent of the properties of the reference and/or test electrodes which are disruptive to measurement; and at least the two test electrodes dip directly into the solution which is to be measured.

According to a second aspect of the invention, there is provided an arrangement for measuring ion concentrations in solutions comprising a container for the solution, at least two ion sensitive test electrodes in said container and having different sensitivities only in respect of the ion or ion mixture to be measured, a reference electrode for providing a signal for setting the operating point of the test electrodes and evaluating means fed with the output of said test electrodes and said reference electrode for producing a measurement result essentially independent of the properties of said reference electrode, and said test electrode which would interfere with accurate measurement.

BRIEF DESCRIPTION OF THE DRAWINGS

The invention will now be described in greater detail, by way of example, with reference to the schematic drawings, in which.

DESCRIPTION OF THE PREFERRED EMBODIMENTS

Figure 1:
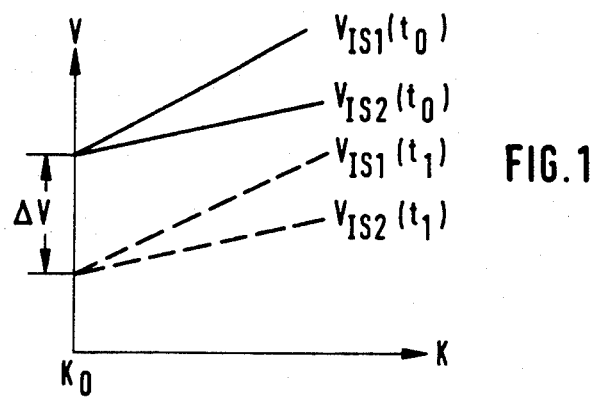
FIG. 1 is a graph illustrating the concept of the invention.

Basically, the invention proposes a method of and apparatus for measuring ion concentrations in solutions using ion-sensitive test and reference electrodes, in which at least two ion-sensitive test electrodes are used, these having different sensitivities to the concentration and/or activity only in relation to the ion or ion mixture to be measured, wherein at least one common reference electrode is used which merely sets at least one operating point of the test electrodes, the output signals of the test electrodes are evaluated such that they are made essentially independent of the properties of the reference and/or test electrodes which are disruptive to measurement, and at least the two test electrodes dip directly into the solution which is to be measured.

A first advantage of the invention is that reference and/or test electrodes with large time fluctuations in their absolute electrical potential can be used without the accuracy and reproducibility of tests on ion concentration being greatly affected. A second advantage is that tests on ion concentration are largely independent in particular of the material and design or construction of the reference and/or test electrodes which can therefore be manufactured simply and cheaply.

A third advantage is that it is possible to dispense to a large extent with time-consuming first and/or intermediate calibration of the device displaying the concentration in the case of exact series measurements The invention is based on the surprising discovery that there are test electrodes which have different sensitivities as compared to the ions which are to be measured, but essentially the same sensitivity to the remaining ions, for example those of the solvent. Such characteristics are described in greater detail with reference to FIG. 1. The concentration K of a type of ion which is to be measured is plotted on the abscissa The ordinate shows the output signal V of two test electrodes IS1, and IS2 respectively, in accordance with the invention. These output signals are designated $V_{IS2}$ and $V_{IS2}$ and, so that the invention can be more easily understood, they are only shown in standardised form such that with the concentration $K_o$ the value of the output signal is the same. Since the test electrodes IS1 and IS2 have different sensitivities as compared to the ions to be measured, at the time $t_o$ the output signals designated $V_{IS1}$ (to) and $V_{IS2}$ (to) respectively, are present, these output signals being dependent on the concentration. If this type of measurement is repeated with the same test electrodes IS1 and IS2, respectively, at a later time $t_1$ then surprisingly the output signals $V_{IS1}(t_1)$ and $V_{IS1}(t_1)$, respectively, which are shown in broken lines, are present and are displaced by substantially the same amount $\Delta V$ as compared to the original output signals. In the case of test electrodes IS1 and IS2, respectively, only the absolute values of the output signals change in the same way and by the same amount, whereas the properties (sensitivity) which depend on the concentration with respect to the ion and/or ion mixture to be measured remain substantially unchanged. Displacement of the output signals by the amount $\Delta V$ during the time difference $\Delta t = t_1 - t_o$ may have a number of causes, for example a change in temperature in the solution or chemical and/or physical variations in the surfaces of the electrodes.

Therefore it is possible to calculate the concentration K of the ion or ion mixture which is to be tested from these output signals $V_{IS1}$ and $V_{IS1}$ in accordance with FIG. 1. This is shown in the following for one of embodiment in which two ion sensitive field effect transistors (ISFETs) are used as the test electrodes and have different sensitivities in relation to an ion which is to be investigated. If an ISFET is operated in the so-called saturation range then the following is true for the drain current $I_D$:

$$I_D = \alpha/2(V_G - V_T)^2$$

In the above $\alpha$ represents a structure and geometry factor, and is defined according to:

$$\alpha = \mu(W/L) \cdot C_o,$$

and is based on the gate width W, the gate length L, of the ISFET, the mobility $\mu$ of the charge carriers in the channel region and the gate capacitance $C_o$. $V_G$ is the electrical voltage applied to the gate of the ISFET, $V_T$ is the voltage at which the ISFET begins to conduct electricity; $V_T$ is generally determined by the semiconductor technique used. These relationships form the basis of the so-called MOS technique. With an ISFET, the gate voltage $V_G$ is not applied to the gate via a metallic layer but with the aid of a reference electrode through a liquid electrolyte. In addition, this gate voltage $V_G$ includes an additional electrical voltage $V_{IS}$ which is formed by the ion sensitivity of the ISFET gate in relation to the ions of the solution which are to be measured, when there is a fixed reference potential $V_{EL}$ at the reference electrode. This additional voltage $V_{IS}$ changes with the ion concentration of the solution. As stipulated, the sensitivity of the two ISFETs is different. Therefore the electrical voltages $V_{IS1}$ and $V_{IS2}$, respectively, which depend on the concentration, can be shown for both ISFETs IS1 and IS2 as Nernst equations modified by the factors $k_1$ and $k_2$, respectively:

$$V_{IS1} = o_1 + k_1 \cdot (RT/zF) \ln a_{Mez+} \text{ for IS1 and} \quad (2)$$

$$V_{IS2} = V_{o2} + k_2 \cdot (RT/zF) \ln a_{Mez+} \text{ for IS2.} \quad (3)$$

$V_{o1}$ and $V_{o2}$ are electrical standard voltages which correspond to the standard potential $\Delta\psi_o$ formula (1).

The drain current at the two ISFETs IS1 and IS2 in question is then $$I_{D1} = (\alpha_1/2)(V_{EL} - V_T + V_{IS1})^2 \text{ for } -\text{IS1 and} \quad (4)$$

$$I_{D2} = (\alpha_2/2)(V_{EL} - V_T + V_{IS2})^2 \text{ for IS2.} \quad (5)$$

If both ISFETs are produced by the same semiconductor technique, then the voltage $V_T$ is identical for both.

In addition, during measurement, the same reference electrode is used for both ISFETs; therefore, the reference potential $V_{EL}$ is also identical. Generally $\alpha_1=\alpha_2$. However, this is not essential, since even if $\alpha_1 \neq \alpha_2$, then it is still possible to provide an advantageous circuit design. The unknown magnitudes $V_{EL}$ and $V_T$ can be eliminated from the two equations (4) and (5) for the drain currents by algebraic conversion such as extracting the root and forming the difference. The result is the formula:

$$V_{IS1} - V_{IS2} = \sqrt{2}\left(\sqrt{\frac{I_{D1}}{\alpha_1}} - \sqrt{\frac{I_{D2}}{\alpha_2}}\right). \tag{6}$$

This difference can be simulated, for example, by means of circuitry. On the other hand it follows from equations (2) and (3) that:

$$V_{IS1} - V_{IS2} = V_{o1} - V_{o2} + (k_1 - k_2)(RT/zF) \ln a_{Mez+} \tag{7}$$

This shows that the measured value is clearly a function of the ion activity $a_{Mez+}$ in the solution and there is no dependency on the potential of the reference electrode. Therefore, it is possible to evaluate the drain currents $I_{D1}$ and $I_{D2}$ in accordance with formulae (6) and (7) with a suitable circuit arrangement (not shown) which includes analog/digital converters, for example, and a so-called microprocessor, such that the concentration and/or the activity of ion or ion mixture to be measured is, for example, displayed directly.

Figure 2:
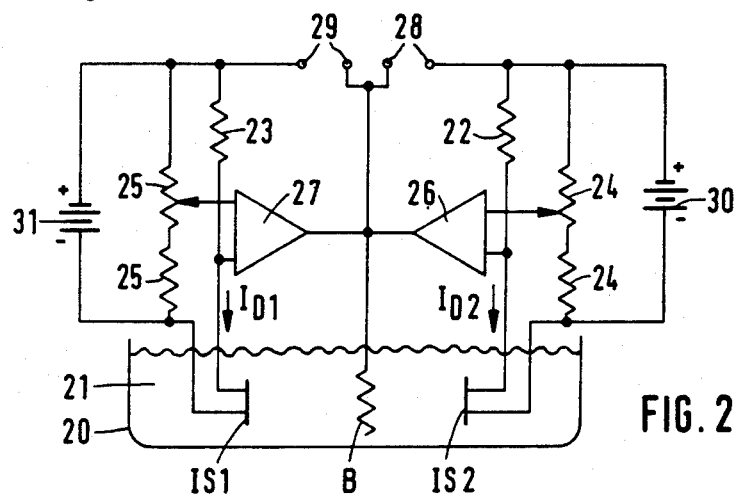
FIG. 2 is a circuit schematic of one embodiment of the invention.

In another embodiment in accordance with FIG. 2, at least one test electrode IS1, IS2—in this embodiment there are also ISFETs—is operated with a substantially constant electric current and the electrical voltages, which are set automatically and depend on the concentration and/or activity, are evaluated.

In an electrically non-conductive vessel 20 filled with an electrolyte 21 to be measured, at least one reference electrode B and two test electrodes IS1 and IS2, ISFETs, for example, are present. In order to obtain a constant drain current $I_{D1}$ or $I_{D2}$ the respective gate voltage—in this case the electrical potential between the reference electrode and a test electrode IS1 or IS2—is adjusted accordingly. In addition the voltage drop across a reference voltage divider 24 or 25, respectively, which is settable, is used for comparison. This comparison is implemented by an operational amplifier 26 or 27, respectively, which adjusts its output voltage until the drain current, changed by the gate voltage, resumes its original value. This change in the output voltage is tapped and evaluated at output terminals 28 and 29, respectively, with the aid of a subtracting arrangement (not shown), for example, or with the aid of electronic data processing (microprocessing). The required supply voltage sources are given the symbols 30 and 31, respectively. The potentials in the two circuits are displaced in similar manner when there is a change in the reference electrodes but differently when there is a change in the ion concentration.

Figure 3:
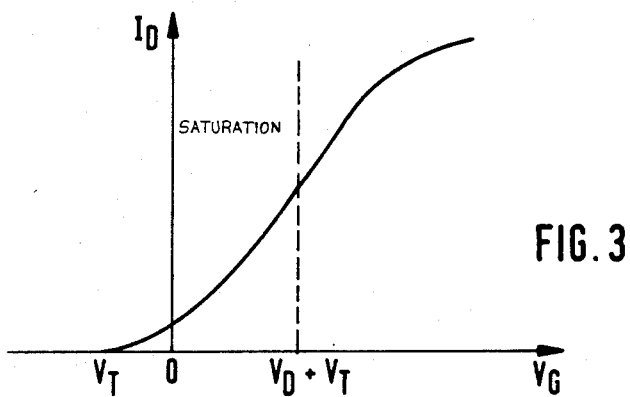
FIG. 3 is a graph of a characteristic curve of a test electrode as used in the embodiment of FIG. 2.

The reference electrode B merely serves to set an operating point for the test electrodes IS1 or IS2. The test result then becomes independent of the electrical reference potential of the reference electrode B and/or of any disruptive electrical potentials of the electrolyte and/or the test electrodes IS1 and IS2, respectively. Therefore, in an embodiment where the vessel 20 is electrically conductive and comprises electrode B, such electrode can be selected largely as desired as long as a predetermined reference potential is present within a value range determined by a predetermined characteristic curve of the test electrodes. If, for example, the ISFETs mentioned are used as the test electrodes IS1 and IS2, respectively, then the characteristic curve essentially follows a path as shown in FIG. 3. In FIG. 3 the drain current $I_D$ of an ISFET is plotted as a function of its gate voltage $V_G$. The term "saturation" designates a region in which the formulae (4) and (5) apply. In the saturation region the drain current $I_D$ of an ISFET is essentially proportional to the square of the electric potential applied to the gate. With ISFETs, the limit of the saturation region, which is shown in broken lines in FIG. 3, is at a gate voltage $V_G$ of approximately 1 V to 10 V. This limit arises from the formula $V_G = V_D + V_T$, $V_D$ and $V_T$ representing the drain voltage and the threshold voltage of the ISFET. The fluctuations in the reference electrode B which are disruptive and were mentioned at the outset are however substantially smaller and generally less than 10 mV. It should be pointed out, therefore, that each of the two ISFETs operates, as compared to the reference electrode, such that a drain current, for example, is set in accordance with the reference potential. The electrical potential of the electrode can therefore vary in the saturation range without greatly affecting the test result obtained by forming the difference. Therefore, the use of exactly manufactured and therefore expensive reference electrodes, which is otherwise necessary, can be dispensed with even in precise electrochemical measurement. Any metal or other optional electrode materials are also suitable for the reference electrodes. In commercial use, for example in domestic appliances, it is possible to use the inner walls of the vessel or metallic tube walls as reference electrodes. Only one requirement is made of the reference electrode: it must allow for a sufficiently high electrical exchange current facilitating a change in the charge of the ISFET gate.

The invention can be used on any desired test electrodes which have different sensitivities for only one ion or ion mixture to be measured but have substantially the same sensitivity for the remaining ions.

A further refinement of the invention lies in compensating for the characteristic curves of test electrodes IS1 and IS2 such that measurement is not limited, for example, only to the said saturation region but is also possible at essentially any desired point on the characteristic curve of the test electrode. This kind of compensation can be effected in a circuit arrangement according to FIG. 2 for example by providing the reference electrode B and the test electrodes IS1 and IS2, respectively, in the feedback branches of the operational amplifiers 27 and 26, respectively. Therefore, characteristic curves in accordance with FIG. 3 and faults having a similar affect on both test electrodes can be compensated for by control circuits designed in this way.

It is possible for an electrical current with a difference current intensity to flow through both test electrodes IS1, IS2 and for both test electrodes to be of slightly different configuration or arrangement, including for example a different distance from the reference electrode because these such differences in configuration and arrangement only affect displacement of the output signals determined by the respective arrangement, for example the voltages at terminals 28,29. This displacement can be determined, for example with a calibrating solution and can therefore be taken into account during measurement and set in a test arrangement in the form of a so-called device constant.

Furthermore, it is possible to operate the test electrodes using d.c. or a.c. current or superimposition of both, for example d.c. current with a superimposed a.c. current component, if this should be necessary for certain measurements. In such a case, the evaluation circuit should be suitable for processing said current.

In the embodiments which have been described, the test electrodes IS1, IS2 for the ions which are to be tested have different sensitivities, produced for example by providing the test electrodes IS1, IS2, ISFET's for example, with ion sensitive gate areas of different size.

In a further embodiment (not shown) test electrodes are used which have the same sensitivities with respect to the ion to be measured when at the same temperature. In accordance with the invention the necessary different sensitivities are produced by maintaining a predetermined (known and/or measurable temperature difference between the test electrodes. Then, in accordance with the Nernst equation (1) as mentioned at the outset, there is also a potential difference $\Delta \psi$ which can be evaluated. The necessary temperature difference can be produced, for example, by heating one of the test electrodes either directly or indirectly by means of an electric current or by maintaining a temperature difference between the test electrodes in the solution to be tested.

It is possible for this sort of temperature difference to bring about an undesirable displacement of the electrical values, for example, displacement of the operating point, of the test electrodes and/or the evaluation circuit connected thereto. This is definable for example, in the form of a calibration curve and can then be taken into account when evaluating the measurements.

It will be understood that the above description of the present invention is susceptible to various modifications, changes and adaptations.

What is claimed is:

1. A method of measuring ion concentrations in solutions, comprising: using at least two-ion sensitive test electrodes, these having different sensitivities to at least one of the concentration and activity only in relation to the ion or ion mixture to be measured, using at least one common reference electrode which merely sets at least one operating point of the test electrodes, evaluating the output signals of the test electrodes by producing a measurement signal which represents the difference between the output signals and which is essentially independent of the properties of at least one of the reference and test electrodes which are disruptive to measurement; and dipping at least the two test electrodes directly into the solution which is to be measured.

2. A method as defined in claim 1 wherein at least two sensitive field effect transistors with different sensitivities are used as the test electrodes and that the output signals of the field effect transistors are essentially evaluated in accordance with the formula:

$$V_{IS1} - V_{IS2} = \sqrt{2}\left(\sqrt{\frac{I_{D1}}{\alpha_1}} - \sqrt{\frac{I_{D2}}{\alpha_2}}\right)$$

$V_{IS1}$, $V_{IS2}$ representing the different sensitivities of the two field effect transistors as compared to the ions which are to be measured, $I_{D1}$, and $I_{D2}$ designate the drain currents of the field effects transistors which are characterised by the structure and geometry factors $\alpha_1$ and $\alpha_2$ respectively.

3. A method as defined in claim 2, wherein a drain current is selected for the purpose of setting the operating point of one of said ion sensitive field effect transistors which is substantially proportional to the square of the electrical voltage applied to the gate of said one ion sensitive field effect transistor.

4. A method as defined in claim 1, wherein at least two test electrodes with different sensitivities are used and each test electrode has delivered thereto an electrical current which is essentially constant.

5. A method as defined in claim 4, wherein an electrical voltage difference which depends essentially on at least one of the concentration and activity of the ion or ion mixture is evaluated and is formed from the electrical voltages which are required to maintain the constant currents.

6. A method as defined in claim 1, wherein an electrically conductive region of a vessel containing the solution is used as the reference electrode.

7. A method as defined in claim 1, wherein a reference electrode is used whose electrical exchange current is greater than that required to change the electrical charge of the test electrodes.

8. A method as defined in claim 1, wherein the difference in the two output signals of said test electrodes is evaluated and produced by an arrangement which includes control circuits for substantially compensating the characteristic curves of said test electrodes so that any point of the respective curves can be utilized to effect the ion concentration measurement.

9. A method as defined in claim 1, wherein at least one said test electrode is operated by one of an electrical direct current, alternating current and superimposition of both a direct and alternating current.

10. A method as defined in claim 9 wherein a difference in at least one of the electrical voltage and current is determined at least once, and including providing means for adjusting the magnitude of said difference when the at least two test electrodes of different sensitivity are inserted into at least one predetermined solution; and such difference is taken into account when taking measurements which depend on at least one of the concentration and activity.

11. Apparatus for carrying out the method as defined in claim 1, including two test electrodes each comprising an ion sensitive field effect transistor having a gate providing a different sensitivity for the ions which are to be measured relative to the sensitivity of the gate of the other field effect transistor.

12. Apparatus as defined in claim 11, and comprising an evaluation circuit having at least one part which is joined together with at least one of said test electrodes to form an integrated component.

13. Apparatus as defined in claim 12, and comprising at least one control circuit for keeping an electrical current flowing through at least one said test electrode essentially constant and evaluating the electrical voltage required for said electrical current.

14. Apparatus as defined in claim 12 and comprising means for establishing a predeterminable temperature difference between said test electrodes for providing different and evaluable sensitivities for the ions to be tested.

15. Apparatus as defined in claim 14, said test electrodes at the same temperature have essentially the same sensitivity to the ions which are to be measured.

16. A method of measuring ion concentration in solutions comprising placing at least two ion sensitive test electrodes having different sensitivities only in respect of the ion or ion mixture to be measured in the solution, setting an operating point of said tests electrodes by means of at least one common reference electrode and evaluating the output signals of said test electrodes to produce a measurement result which represents the difference between the output signals and which is essentially independent of properties of said reference and test electrodes which would interfere with accurate measurement.

17. An arrangement for measuring ion concentrations in solutions comprising a container for the solution, at least two ion sensitive test electrodes in said container and for producing respective output signals, said test electrodes having different sensitivities only in respect of the ion or ion mixture to be measured, a reference electrode for providing a signal for setting the operating point of the test electrodes and evaluating means fed with the output signals of said test electrodes for producing a measurement result which represents the difference between the output signals and which is essentially independent of properties of said reference electrode and said test electrode which would interfere with accurate measurement.

* * * * *